United States Patent
Suzuki et al.

(10) Patent No.: US 6,395,857 B1
(45) Date of Patent: May 28, 2002

(54) MODIFIED ORGANOPOLYSILOXANES, PRODUCTION THEREOF AND COMPOSITIONS

(75) Inventors: Takanao Suzuki; Daisuke Tsukioka, both of Chiba; Hiroyuki Ohno; Natsue Kawahara, both of Toyko, all of (JP)

(73) Assignee: Chiba Flour Milling Co. Ltd., Chiba (JP)

( * ) Notice: Subject to any disclaimer, the term of this patent is extended or adjusted under 35 U.S.C. 154(b) by 0 days.

(21) Appl. No.: 09/575,990

(22) Filed: May 23, 2000

(30) Foreign Application Priority Data

May 24, 1999 (JP) .......................................... 11-143184

(51) Int. Cl.[7] .............................................. C08G 77/06
(52) U.S. Cl. .............................. 528/27; 528/26; 528/38
(58) Field of Search ............................... 528/26, 27, 38

(56) References Cited

U.S. PATENT DOCUMENTS 3,773,607 A * 11/1973 Marzocchi
4,515,702 A  5/1985 Mori et al. ................. 252/49.6
4,973,620 A  11/1990 Ona et al. .................... 524/292
5,712,391 A  1/1998 Ohno et al. .................. 544/194

FOREIGN PATENT DOCUMENTS

JP   2000063747 A  *  2/2000

* cited by examiner

Primary Examiner—Robert Dawson
Assistant Examiner—Marc S. Zimmer
(74) Attorney, Agent, or Firm—David G. Conlin; John B. Alexander; Edwards & Angell, LLP

(57) ABSTRACT

A modified organopolysiloxane in which a carboxyl group of a heterocyclic compound having a carboxyl group and containing a nitrogen atom as a heteroatom is combined with an amino group of an amino-modified silicone is used as a gelling agent for low-viscosity silicone oil, which can allow the low-viscosity silicone oil to stably gel without losing the characteristics thereof.

8 Claims, 2 Drawing Sheets

MODIFIED ORGANOPOLYSILOXANES, PRODUCTION THEREOF AND COMPOSITIONS

FIELD OF THE INVENTION

The present invention relates to modified organopolysiloxanes and compositions containing them. More particularly, the invention relates to compounds in which carboxyl groups of heterocyclic compounds are combined with amino groups of amino-modified silicones, and compositions containing the above-described compounds and silicone oil. The above-mentioned compounds can thicken silicone oil and allow the silicone oil to gel, so that they can impart stability to products using the silicone oil and improve feeling and usability thereof. They can be therefore used in various industrial products, pharmaceutical preparations and cosmetics.

BACKGROUND OF THE INVENTION

Recently, silicone oil, particularly low-viscosity silicone oil, has been compounded in many cosmetics because of its excellent extensibility, refreshing feeling, lubricity, water repellency and high safety.

However, silicone oil is generally poor in compatibility with other oils, so that it is difficult to prepare stable products containing it. Even when wax is added for obtaining stable gelatinous or emulsion-like products using the low-viscosity silicone oil as bases, stable products are not obtained. The use of crosslinked silicones raises the problem that sticky feeling remains while inherent refreshing feeling of the silicone oil is lost.

Then, stable bases have been desired which can allow the low-viscosity silicone oil to gel without impairing the inherent excellent extensibility and refreshing feeling thereof and which can be obtained by simple compounding, and in which the low-viscosity silicone oil is not separated and not discharged from the resulting compositions.

SUMMARY OF THE INVENTION

As a result of intensive investigation under such situations, the present inventors have discovered that modified organopolysiloxanes in which carboxyl groups of heterocyclic compounds are combined with amino groups of amino-modified silicones can allow silicone oil to stably gel, thus completing the invention.

That is to say, the invention provides:

(1) A modified organopolysiloxane in which a carboxyl group of a heterocyclic compound having a carboxyl group and containing a nitrogen atom as a heteroatom is combined with an amino group of an amino-modified silicone;

(2) The modified organopolysiloxane described in (1), in which the heterocyclic compound is a 6-membered heteromonocyclic compound;

(3) The modified organopolysiloxane described in (2), in which the 6-membered heteromonocyclic compound is orotic acid:

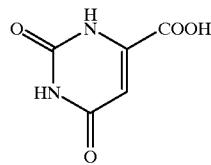

(4) The modified organopolysiloxane described in (2), in which the 6-membered heteromonocyclic compound is pyridinecarboxylic acid:

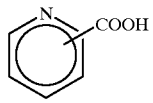

(5) The modified organopolysiloxane described in (1), (2), (3) or (4), in which the amino-modified silicone is a silicone represented by formula (3):

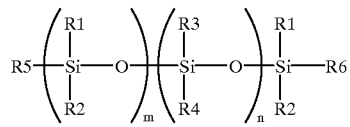

wherein R1 to R3, which may be the same or different, represent alkyl groups each having 1 to 22 carbon atoms, phenyl groups, naphthyl groups or polyoxyalkylene groups; at least one of R4 to R6 is a group represented by formula (4):

(wherein R7 and R8 represent alkylene groups each having 1 to 6 carbon atoms, and S represents 0 or 1), and the remaining groups, which may be the same or different, represent alkyl groups each having 1 to 22 carbon atoms, phenyl groups, naphthyl groups or polyoxyalkylene groups; and m and n each represent numbers of 1 or more;

(6) A method for producing the modified organopolysiloxane described in (1), (2), (3), (4) or (5), which comprises reacting a heterocyclic compound having a carboxyl group and containing a nitrogen atom as a heteroatom with an amino-modified silicone in water;

(7) A method for producing the modified organopolysiloxane described in (1), (2), (3), (4) or (5), which comprises reacting a heterocyclic compound having a carboxyl group and containing a nitrogen atom as a heteroatom with an amino-modified silicone in a mixture of water and silicone oil;

(8) A composition comprising the modified organopolysiloxane described in (1), (2), (3), (4) or (5) and silicone oil;

(9) An emulsion composition obtained by reacting a heterocyclic compound having a carboxyl group and containing a nitrogen atom as a heteroatom with an amino-modified silicone in water and silicone oil, and stirring the resulting system; and

(10) A gelling agent which is consisted of the modified organopolysiloxane in (1) to (5).

DESCRIPTION OF THE PREFERRED EMBODIMENTS

Figure 1:
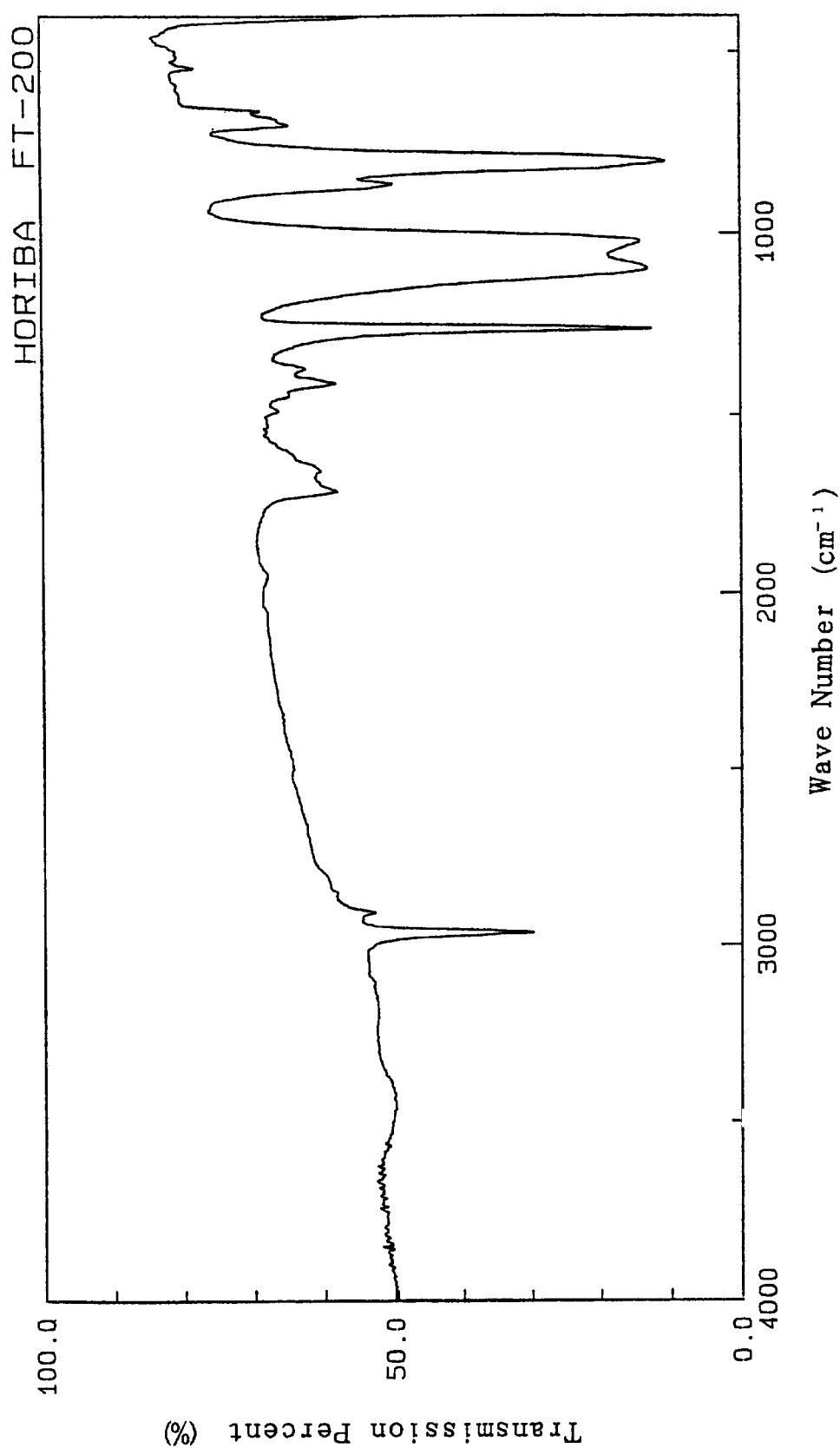
FIG. 1 is a graph showing an infrared absorption spectrum of a compound obtained in Example 1.

The invention will be described in detail below. The heterocyclic compounds having a carboxyl group and containing a nitrogen atom as heteroatom used in the invention include heteropolycyclic compounds each having a plurality of rings, as well as heteromonocyclic compounds each having a single ring. The heteromonocyclic compounds include 5- to 7-membered cyclic compounds. Of these, the 6-membered heteromonocyclic compounds are preferred. The carboxyl group may be bound to the ring directly or with the interposition of a methylene or ethylene group. Among the heterocyclic compounds which can be used in the invention, the 5-membered heteromonocyclic compounds each containing one nitrogen atom as a heteroatom include proline, 4-hydroxyproline and 1-pyroglutamic acid, and the 6-membered heteromonocyclic compounds each containing one nitrogen atom as a heteroatom include pyridinecarboxylic acids such as picolinic acid, nicotinic acid and isonicotinic acid, fusaric acid, pipecolic acid, aminonicotinic acid, nipecotic acid and citrazinic acid. The 6-membered heteromonocyclic compounds each containing two nitrogen atoms include orotic acid and 2-pyrazinecarboxylic acid, and the 6-membered heteromono-cyclic compounds each containing three nitrogen atoms include oxonic acid. Further, the heteropolycyclic compounds include heteropolycyclic compounds each containing one nitrogen atom such as kynurenic acid, quinaldinic acid and xanthurenic acid. However, the heterocyclic compounds usable in the present invention are not limited to these compounds.

The amino-modified silicones used in the present invention include silicones having amino groups at one or both ends thereof and/or on side chains thereof. They are represented by the following general formula:

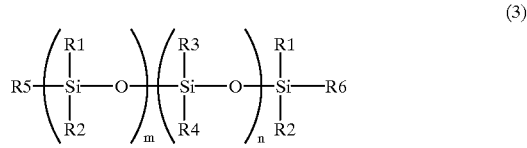

(3)

wherein R1 to R3, which may be the same or different, represent alkyl groups each having 1 to 22 carbon atoms, phenyl groups, naphthyl groups or polyoxyalkylene groups (wherein the alkylene preferably has 2 to 4 carbon atoms and the average polymerization degree is 1 to 50); at least one of R4 to R6 is a group represented by formula (4):

(4)

(wherein R7 and R8 represent alkylene groups each having 1 to 6 carbon atoms, and S represents 0 or 1), and the remaining groups, which may be the same or different, represent alkyl groups each having 1 to 22 carbon atoms, phenyl groups, naphthyl groups or polyoxyalkylene groups (wherein the alkylene preferably has 2 to 4 carbon atoms and the average polymerization degree is 1 to 50); and m and n each represent integers of 1 or more.

The both-end amino-modified silicones include BY16-853B (manufactured by Dow Corning Toray Silicone Co., Ltd.), X-22-161A (manufactured by Shin-Etsu Chemical Co., Ltd.) and OF-204-60 (manufactured by Nippon Unicar Company Limited), and the side-chain amino-modified silicones include BY16-872 (manufactured by Dow Corning Toray Silicone Co., Ltd.), KF393 and KF864 (manufactured by Shin-Etsu Chemical Co., Ltd.) and FZ-3705 (manufactured by Nippon Unicar Company Limited). Further, when the silicones having polyoxyalkylene groups as R1 to R6 are used, the resulting products have excellent properties as emulsifiers, and specific examples thereof include X-22-3939A (manufactured by Shin-Etsu Chemical Co., Ltd.).

The amino equivalent (the molecular weight per molecule of amino group) of the amino-modified silicone to be used is from 300 to 20,000, and preferably from 1,000 to 12,000. When the amino equivalent is less than 300, the modified organopolysiloxanes obtained by reaction with the heterocyclic compounds become impossible to disperse in the silicone oil, resulting in failure to exhibit the thickening and gelation ability. On the other hand, when the amino equivalent exceeds 20,000, the thickening and gelation ability of the modified organopolysiloxanes obtained by reaction with the heterocyclic compounds is deteriorated.

The reaction of the heterocyclic compounds with the amino-modified silicones can be conducted by stirring both without solvents. However, the use of solvents is preferred for more uniformly reacting the heterocyclic compounds with the amino-modified silicones. Examples of the solvents used include organic solvents such as benzene, n-hexane, chloroform, dimethylformamide, ethanol and methanol, water, cyclic silicones such as octamethylcyclotetrasiloxane and decamethylcyclopentasiloxane, chain silicones such as dimethylpolysiloxane, and silicone oil such as methylphenylpolysiloxane. Water, silicone oil and a mixture of water and silicone oil are preferably used. The use of water and/or silicone oil in the reaction has the advantages that the safety is extremely high even when the solvents are only partially removed after the reaction, and that the reaction products can even be used as bases for cosmetics and others without removal of the solvents, in contrast with the use of the other organic solvents. Using these solvents, the heterocyclic compounds and the amino-modified silicones are stirred at room temperature or with heating for several minutes to several hours to react with each other. After the reaction, the organic solvents are removed by evaporation under reduced pressure, or water is removed by lyophilization to obtain the modified organopolysiloxanes (hereinafter briefly referred to as "synthesized products").

As to the synthesized products of the invention, products different in form such as viscous products, gelatinous products and white powdery products can be obtained by varying the viscosity and the amino equivalent of amino-modified silicone and the kind of heterocyclic compound. When the amino equivalent is low, the products become powdery. On the other hand, when the amino equivalent is high, the products become gelatinous to viscous. Accordingly, gels of various forms from a soft gelatinous form to a hard resinous form can be obtained by appropriately selectively adding these synthesized products to silicone oil used as bases for cosmetics.

The silicone oil used in the compositions containing the synthesized products of the invention and the silicone oil may be any, as long as it is liquid. The silicone oil is the same as that used as the above-mentioned solvents, and includes, for example, cyclic silicones such as octamethylcyclotetrasiloxane and decamethylcyclopentasiloxane, chain silicones such as dimethylpolysiloxane, and silicone oil such as methylphenylpolysiloxane. The compositions can also be used as various industrial products, and bases for pharmaceutical preparations, as well as bases for cosmetics.

When water and the silicone oil are used in the reaction of the method of the invention, emulsion compositions of water and the silicone oil can be obtained by stirring this system after the reaction. The system can be stirred by the use of a propeller or a homomixer. The emulsion compositions can be directly used as the bases for cosmetics.

The invention will be described in more detail with the following examples, but it is understood of course that they are not intended to limit the scope of the invention.

EXAMPLE 1

Eleven grams of a both-end amino-modified silicone (amino equivalent: 2,200, viscosity: 100 cSt/25° C.) and 872 mg of orotic acid monohydrate were dispersed in 250 ml of water and 44 g of decamethylcyclopentasiloxane, and the resulting dispersion was stirred at room temperature for 5 hours. Then, water was removed by lyophilization, the reaction product was extracted with chloroform, whereby unreacted orotic acid was removed by precipitation, followed by evaporation under reduced pressure, thus obtaining 10.8 g of a colorless and clear gelatinous material.

Figure 2:
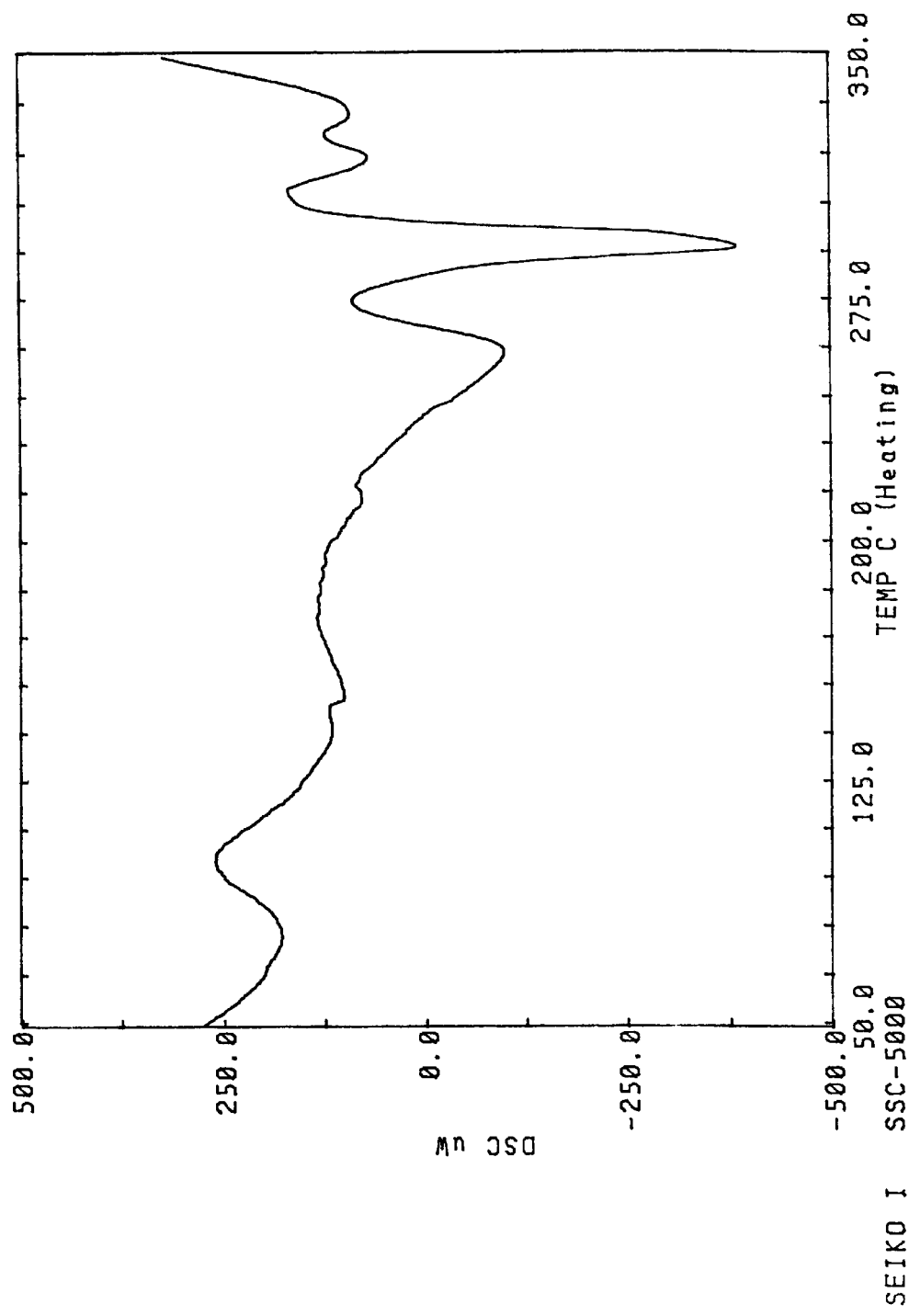
FIG. 2 is a graph showing a differential scanning thermal analysis diagram of the compound obtained in Example 1.

An infrared absorption spectrum of the gelatinous material (measured with an FT-200 Fourier transform infrared spectrometer manufactured by Horiba Ltd.) is shown in FIG. 1, and a differential scanning thermal analysis diagram thereof (measured with a DSC100 differential scanning calorimeter manufactured by Seiko Instruments Inc.) is shown in FIG. 2. Orotic acid used as the raw material was not contained at all in the chloroform extract in this example because of its poor solubility. However, the absorption (1650 $cm^{-1}$ to 1750 $cm^{-1}$) derived from the starting orotic acid and the absorption (800 $cm^{-1}$ to 1300 $cm^{-1}$) derived from the starting amino-modified silicone were confirmed in FIG. 1, and a novel endothermic peak which is not observed for orotic acid and the amino-modified silicone used as the raw materials was further confirmed between 215° C. and 335° C. These facts indicate that the reaction of both the starting materials occurred.

The solubility (10% by weight) of the gelatinous material in various solvents is shown in Table 1. 10 g of the gelatinous material was added to 90 g of a solvent and the gelatinous material was dissolved into this solvent with or without heat. The state after dissolution was observed in each case.

TABLE 1

| Chloroform | Not gelled after dissolution |
| Benzene | Not gelled after dissolution |
| Decamethylcyclopentasiloxane | Gelled after dissolution |
| Octamethylcyclotetrasiloxane | Gelled after dissolution |

EXAMPLES 2 and 3

Each both-end amino-modified silicone shown in Table 2 and orotic acid were reacted with each other under conditions shown in Table 2, followed by lyophilization in Example 2 or evaporation under reduced pressure in Example 3 to obtain a synthesized product. The form of the resulting synthesized products and the solubility thereof in various solvents are shown in Tables 3 and 4.

TABLE 2

| Example | Both-End Amino-Modified Silicone | | | Orotic Acid Monohydrate Weight | Solvent | Conditions |
|---|---|---|---|---|---|---|
| | Viscosity | Amino Equivalent | Weight | | | |
| 2 | 15 | 470 | 2.35 g | 872 mg | Water 50 ml | Room temp. 5 hrs |
| 3 | 290 | 4,600 | 4.6 g | 174 mg | Ethanol 100 ml | Room temp. 5 hrs |

TABLE 3

| Example | Form | Yield |
|---|---|---|
| 2 | Powder | 3.2 g |
| 3 | Soft gelatinous | 4.6 g |

TABLE 4

| | Example 2 | Example 3 |
|---|---|---|
| Chloroform | Not gelled after dissolution | Not gelled after dissolution |
| Benzene | Not gelled after dissolution | Not gelled after dissolution |
| Decamethylcyclopentasiloxane | Gelled after dissolution | Gelled after dissolution |
| Octamethylcyclotetrasiloxane | Gelled after dissolution | Gelled after dissolution |

EXAMPLES 4 to 7

Each side-chain amino-modified silicone shown in Table 5 and picolinic acid were added to 50 ml of each solvent shown in Table 5, and the resulting mixture was stirred for 5 hours, followed by evaporation under reduced pressure to obtain a picolinic acid-modified organopolysiloxane. The form of the resulting synthesized products and the solubility thereof in various solvents are shown in Tables 5 and 6.

TABLE 5

| Example | Amino-Modified Silicone Viscosity | Amino Equivalent | Weight | Picolinic Acid Weight | Solvent | Temp. | Yield | Form |
|---|---|---|---|---|---|---|---|---|
| 4 | 60 | 360 | 1.8 g | 616 mg | Benzene | Room temp. | 2.4 g | Powder |
| 5 | 120 | 1,800 | 9 g | 616 mg | Methanol | Room temp. | 9.6 g | Soft gel |
| 6 | 1,200 | 1,800 | 9 g | 616 mg | Methanol | Room temp. | 9.6 g | Hard gel |
| 7 | 20,000 | 1,800 | 9 g | 616 mg | Hexane | 40° C. | 9.6 g | Soft gel |

TABLE 6

| Example | 4 | 5 | 6 | 7 |
|---|---|---|---|---|
| Chloroform | Δ | Δ | Δ | Δ |
| Benzene | Δ | Δ | Δ | Δ |
| Decamethylcyclopentasiloxane | ⊙ | ○ | ⊙ | ○ |
| Octamethylcyalotetrasiloxane | ○ | Δ | ○ | Δ |

⊙ Hard gel after dissolution
○ Soft gel after dissolution
Δ Not gelled after dissolution
X Not dissolved

EXAMPLE 8

2.3 g of a both-end amino-modified silicone (72 cSt/25° C. amino equivalent: 2,300) and 124 mg of 2-pyrazinecarboxylic acid were dissolved into 50 ml of ethanol, and reacted with each other at room temperature for 5 hours, followed by evaporation under reduced pressure to obtain 2.4 g of a colorless and clear gel. The solubility of the synthesized product in various solvents is shown in Table 7.

EXAMPLE 9

9 g of a both-end amino-modified silicone (120 cSt/25° C. amino equivalent: 1,800) and 866 mg of quinaldinic acid were dissolved into 50 ml of ethanol, and reacted with each other at room temperature for 5 hours, followed by evaporation under reduced pressure to obtain 9.8 g of a colorless and clear gel. The solubility of the synthesized product in various solvents is shown in Table 7.

EXAMPLE 10

9 g of a both-end amino-modified silicone (1,200 cSt/25° C. amino equivalent: 1,800) and 866 mg of quinaldinic acid were dissolved into 50 ml of benzene, and reacted with each other at 40° C. for 2 hours, followed by evaporation under reduced pressure to obtain 9.8 g of a colorless and clear gel. The solubility of the synthesized product in various solvents is shown in Table 7.

TABLE 7

| Example | 8 | 9 | 10 |
|---|---|---|---|
| Chloroform | Δ | Δ | Δ |
| Benzene | Δ | Δ | Δ |
| Decamethylcyclopentasiloxane | ⊙ | ○ | ⊙ |
| Octamethylcyclotetrasiloxane | ⊙ | Δ | ○ |

⊙ Hard gel after dissolution
○ Soft gel after dissolution
Δ Not gelled after dissolution
X Not dissolved The properties of decamethylcyclopentasiloxane gels (10% by weight) of the synthesized products of Examples 1 to 10 are shown in Table 8.

TABLE 8

| | Properties of Gel (1) | |
|---|---|---|
| Example | Extension | Stability |
| 1 | ⊙ | ⊙ |
| 2 | ○ | ⊙ |
| 3 | ⊙ | ⊙ |
| 4 | ○ | ⊙ |
| 5 | ⊙ | ⊙ |
| 6 | ○ | ⊙ |
| 7 | ⊙ | ⊙ |
| 8 | ○ | ⊙ |
| 9 | ⊙ | ⊙ |
| 10 | ○ | ⊙ |

Extension ⊙: Very good
○: Good
Δ: Not so good
X: Not dissolved
Stability ⊙: Stable
○: Practically stable
Δ: A solvent comes to the surface
X: Separated
Gel (1): Decamethylcyclopentasiloxane gel

EXAMPLE 11

Eleven grams of a both-end amino-modified silicone (100 cSt/25° C. amino equivalent: 2,200) and 872 mg of orotic acid monohydrate were added to 250 ml of water and 44 g of decamethylcyclopentasiloxane, and the resulting mixture was stirred with a homomixer (T. K. AUTO HOMO MIXER, manufactured by Tokushu Kika Kogyo Co., Ltd.) at room temperature at 3,000 rpm for 5 hours to obtain an emulsion. This emulsion was allowed to stand at 5° C. and 40° C. for 24 hours, and the stability and "extension" thereof were evaluated.

TABLE 9

|  | Extension | Stability |
|---|---|---|
| Standing at 5° C. | ◎ | ◎ |
| Standing at 40° C. | ◎ | ○ |

Extension ◎: Very good
○: Good
Δ: Not so good
X: Not dissolved
Stability ◎: Stable
○: Practically stable
Δ: A solvent comes to the surface
X: Separated The modified organopolysiloxanes of the invention in which carboxyl groups of the heterocyclic compounds having the carboxyl groups and containing nitrogen atoms as heteroatom are combined with amino groups of the amino-modified silicones are gelling agents which can allow the low-viscosity silicone oil to gel without impairing the inherent excellent extensibility and refreshing feeling thereof by simple compounding, and give stable compositions in which the low-viscosity silicone oil is not separated and not discharged from the resulting compositions. The modified organopolysiloxanes of the invention provide the prominent effects that have never been achieved by the conventional gelling agents.

What is claimed is:

1. A modified organopolysiloxane in which a carboxyl group of a heterocyclic compound having a carboxyl group and containing a nitrogen atom as a heteroatom is combined with an amino group of an amino-modified silicone wherein the amino-modified silicone is a silicone represented by formula (3):

$$R5\left(\begin{array}{c}R1\\|\\Si-O\\|\\R2\end{array}\right)_m\left(\begin{array}{c}R3\\|\\Si-O\\|\\R4\end{array}\right)_n\begin{array}{c}R1\\|\\Si-R6\\|\\R2\end{array} \quad (3)$$

wherein R1 to R3, which may be the same or different, represent alkyl groups each having 1 to 22 carbon atoms, phenyl groups, naphthyl groups or polyoxyalkylene group; at least one of R4 to R6 is a group represented by formula (4):

$$H_2N-(R7-NH)_s-R8- \quad (4)$$

(wherein R7 and R8 represent alkylene groups each having 1 to 6 carbon atoms, and s represents 0 or 1), and the remaining groups, which may be the same or different, represent alkyl groups each having 1 to 22 carbon atoms, phenyl groups, naphthyl groups or polyoxyalkylene groups;

m represents a number of 2 or more; and
n represents a number of 1 or more.

2. The modified organopolysiloxane according to claim 1, in which the heterocyclic compound is a 6-membered heteromonocyclic compound.

3. A modified organopolysiloxane in which a carboxyl group of a 6-membered heteromonocyclic compound having a carboxyl group and containing a nitrogen atom as a heteroatom is combined with an amino group of an amino-modified silicone in which the 6-membered heteromonocyclic compound is orotic acid:

$$(1)$$

4. The modified organopolysiloxane according to claim 2, in which the 6-membered heteromonocyclic compound is pyridinecarboxylic acid:

$$(2)$$

5. The modified organopolysiloxane according to claim 3, in which the amino-modified silicone is a silicone represented by formula (3):

$$R5\left(\begin{array}{c}R1\\|\\Si-O\\|\\R2\end{array}\right)_m\left(\begin{array}{c}R3\\|\\Si-O\\|\\R4\end{array}\right)_n\begin{array}{c}R1\\|\\Si-R6\\|\\R2\end{array} \quad (3)$$

wherein R1 to R3, which may be the same or different, represent alkyl groups each having 1 to 22 carbon atoms, phenyl groups, naphthyl groups or polyoxyalkylene group; at least one of R4 to R6 is a group represented by formula (4):

$$H_2N-(R7-NH)_s-R8- \quad (4)$$

(wherein R7 and R8 represent alkylene groups each having 1 to 6 carbon atoms, and S represents 0 to 1), and the remaining groups, which may be the same or different, represent alkyl groups each having 1 to 22 carbon atoms, phenyl groups, naphthyl groups or polyoxyalkylene groups; and m and n each represent numbers of 1 or more.

6. A method for producing the modified organopolysiloxane according to claim 1, 2, 3, 4 or 5, which comprises reacting a heterocyclic compound having a carboxyl group and containing a nitrogen atom as a heteroatom with an amino-modified silicone in water.

7. A method for producing the modified organopolysiloxane according to claim 1, 2, 3, 4 or 5, which comprises reacting a heterocyclic compound having a carboxyl group and containing a nitrogen atom as a heteroatom with an amino-modified silicone in a mixture of water and silicone oil.

8. A gelling agent which is consisted of the modified organopolysiloxane of anyone of claims 1 to 5.

* * * * *